United States Patent [19]

Takaishi et al.

[11] Patent Number: 4,465,866
[45] Date of Patent: Aug. 14, 1984

[54] PREPARATION PROCESS OF 2-HYDROXY-3-ALKOXYPROPYLGLYCERYL ETHER

[75] Inventors: Naotake Takaishi, Utsunomiya; Kouichi Urata, Ichikai, all of; Yoshiaki Inamoto, Utsunomiya, all of Japan

[73] Assignee: Kao Soap Co., Ltd., Tokyo, Japan

[21] Appl. No.: 375,224

[22] Filed: May 5, 1982

[30] Foreign Application Priority Data

May 28, 1981 [JP] Japan .................................. 56-81456

[51] Int. Cl.$^3$ ...................... C07C 43/11; C07D 317/00
[52] U.S. Cl. .................................... 568/618; 549/453; 568/623
[58] Field of Search ................. 568/618, 623; 549/453

[56] References Cited

U.S. PATENT DOCUMENTS

| 2,038,705 | 4/1936 | Baldwin et al. | 549/372 X |
| 3,201,420 | 8/1965 | Fuzeu et al. | 568/623 |
| 3,651,090 | 3/1972 | Hardie et al. | 549/451 |
| 4,298,764 | 11/1981 | Berkowitz | 568/618 |

FOREIGN PATENT DOCUMENTS 43966 1/1982 European Pat. Off. ............ 568/672
2020702 11/1979 United Kingdom .

OTHER PUBLICATIONS

H. Meerwein: Houben–Weyl, Methods of Organic Chemistry, vol. 6/3, pp. 40–43.

Primary Examiner—Ethel G. Love
Attorney, Agent, or Firm—Oblon, Fisher, Spivak, McClelland & Maier

[57] ABSTRACT

Some 4-(2'-hydroxy-3'-alkoxy)propoxymethyl-1,3-dioxolanes are prepared by reacting alkylglycidyl ethers with acetal or ketal derivatives of glycerol in the presence of an acidic or basic catalyst. Also disclosed is a process for preparing certain 2-hydroxy-3-alkoxypropylglyceryl ethers, which process comprises subjecting the 4-(2'-hydroxy-3'-alkoxy)propoxymethyl-1,3-dioxolanes to hydrolysis. The above processes can afford intended reaction products with good yield without need for any special post-reaction treatment.

5 Claims, No Drawings

PREPARATION PROCESS OF 2-HYDROXY-3-ALKOXYPROPYLGLYCERYL ETHER

BACKGROUND OF THE INVENTION

This invention relates to a preparation process of a 2-hydroxy-3-alkoxypropylglyceryl ether or the like, and more specifically to a preparation process of a 2-hydroxy-3-alkoxypropylglyceryl ether represented by the general formula (IV):

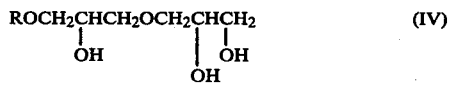

wherein R represents a saturated or unsaturated, straight or branched chain, aliphatic hydrocarbon group having 8–24 carbon atoms (may be abbreviated as "α-monoalkyl ether of diglycerol" later in the present specification) and its synthetic intermediate, 4-(2'-hydroxy-3'-alkoxy)propoxymethyldioxolane represented by the general formula (III):

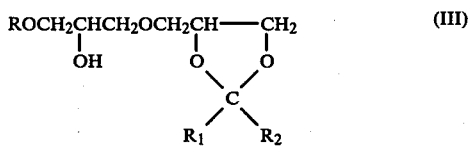

wherein $R_1$ and $R_2$ are individually a hydrogen atom or a lower alkyl, aryl or aralkyl group (may hereinafter be abbreviated as "1,3-dioxolane compound").

In the natural world, there are a number of polyalcohol derivatives containing one or more ether bonds, among which monoalkyl ethers of glycerol (called "glyceryl ethers") are particularly well-known. For example, fish lipid contains palmityl glyceryl ether (chimyl alcohol), stearyl glyceryl ether (batyl alcohol) and oleyl glyceryl ether (selachyl alcohol).

These glyceryl ethers have found wide-spread commercial utility, particularly, as cosmetics bases and the like owing to their W/O-type emulsification characteristics (see, for example, Japanese Patent Laid-open Nos. 87612/1974, 92239/1974 and 12109/1977). Besides, it has been known that they have pharmacological effects such as erythropoietic stimmulating effect for bone marrow, antiinflammatory effect and antitumor activities (see, Japanese Patent Publication Nos. 10724/1974 and, especially, 18171/1977).

Taking into consideration that such glyceryl ethers are unique surfactants having many characteristic features, many attempts have been made to derive polyol ether compounds having a molecular structure analogeous to those of glyceryl ethers (in other words, containing one or more ether bonds and hydrophilic OH-groups therein) from polyalcohols (see, for example, U.S. Pat. No. 2,258,892; Japanese Patent Publication No. 18170/1977 and Japanese Patent Laid-open Nos. 137905/1978 and 145224/1979). The thus-obtained polyol ether compounds are used as cosmetics bases (see, West German Patent Laid-open No. 2,455,287) and general emulsifiers (owing to their W/O-type emulsification characteristics) and also as antimicrobial and fungicidal agents.

As preparation processes of such polyol ether compounds, there have heretofore been known, roughly divided, the following three types of preparation processes:

(1) A polyalcohol is reacted in the presence of an acid or basic catalyst with an alkyl glycidyl ether (I);

(2) An alkali metal alcoholate is formed from a polyalcohol (VI) in the presence of an alkaline substance and the resultant alkali metal alcoholate is reacted with an alkyl halide or the like; and (3) An alcohol (VII) is reacted in the presence of an acid or basic catalyst with an epoxide compound (V) of the 1,3-dioxolane type and the resultant addition product (III') is subjected to hydrolysis (see, Journal f. Prakt. Chemie, Band 316, 325–336 (1974)).

The above processes may be represented by the following chemical equations:

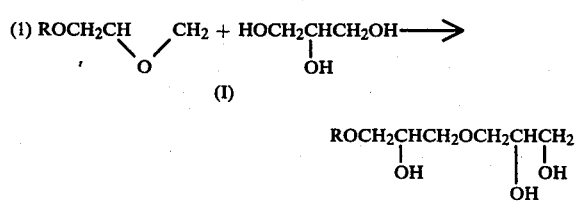

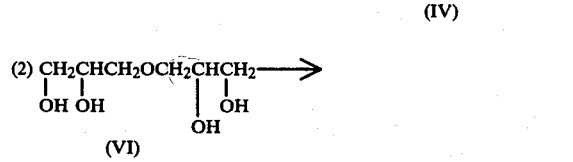

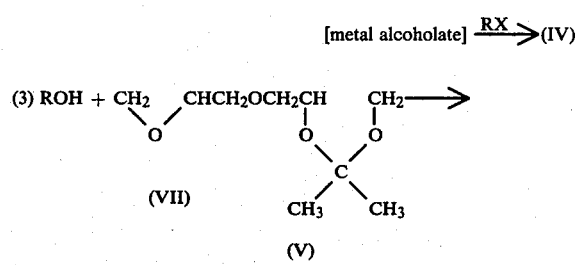

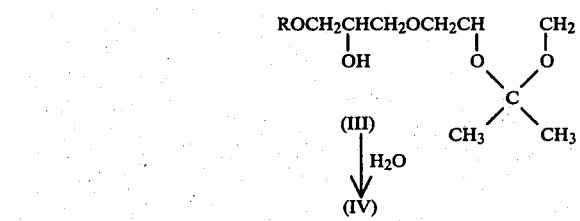

wherein, X represents a halogen atom and R has the same meaning as defined above.

However, these conventional processes are accompanied by the following drawbacks, whereby making it extremely difficult to selectively produce polyol ether compounds in an industrial scale:

(a) First of all, there may be mentioned the extremely poor selectivity of the reaction in each of the processes. Thus, the yield and purity of the intended compound (IV) are limited to extremely low levels in the overall reaction products, whereby deleteriously affecting its physical and chemical properties and making it difficult to provide the intended compound (IV) of uniform quality. The processes (1) and (2) produce, besides the intended ether compound (IV), position isomers of the monoalkyl ether and a mixture which comprises ether compounds substituted by various numbers of alkyl groups such as dialkyl ether and trialkyl ether, because the polyalcohol contains many reactive primary and secondary OH-groups in the same molecule (for example, glycerol in the reaction formula (1) contains two primary OH-groups and one secondary OH-group while diglycerol in the reaction formula (2) has two primary OH-groups and two secondary OH-groups) and these OH-groups may individually take a part in the reaction substantially at the same velocity.

Hence, it is necessary to go through another step such as distillation in order to isolate the intended compound from the reaction product mixture, leading to an irksome process and preventing its adoption in an industrial scale. The process (3) yields, on the other hand, many by-products in addition to the intended addition product (III') due to occurrence of many side reactions, whereby leading to a drawback that its selectivity is considerably lowered. The present inventors attempted to confirm the structure of an α-monoalkyl ether of diglycerol according to this invention, by preparing the ether in accordance with the process (3). As a matter of fact, the intended addition product (III') was obtained with an extremely low yield, i.e., about 30% where a basic catalyst was employed and about 35% or so when an acidic catalyst was used (see, Comparative Examples 3, 4 and 5);

(b) To improve the selectivity of the reaction mentioned in the above item (a), some measures have been taken including using the polyalcohol or monoalcohol excessively or using a special polar solvent to keep the reaction system uniform. However, the incorporation of such measures in an industrial scale is certainly impractical because it is necessary to recover and recycle the polyalcohol used excessively and the use of such a special polar solvent leads to a higher production cost and involves difficult handling of the same; and (c) in order to isolate the intended compound (IV) from the mixture as mentioned in the above item (a), it is contemplated to, in addition to the distillation, protect any free OH-groups through a chemical reaction, separate and collect the thus OH-protected compound and then to remove the protecting groups. However, this results in an increased reaction steps or a cumbersome and complex process. It is thus difficult to practice such a process in an industrial scale.

SUMMARY OF THE INVENTION

The present inventors have carried out an extensive research with a view toward completing a process which provides a highly pure α-monoalkyl ether of diglycerol with a high yield and is free of such drawbacks of the conventional processes. As a result, they have found a process for synthesizing an intended α-monoalkyl ether of diglycerol (IV) of high purity with a high yield by reacting in the presence of a basic or acidic catalyst an alkylglycidyl ether (1), which can be readily produced from its corresponding alcohol, with a glycerol which is protected at its 2-position and 3-position by suitable protecting groups, namely, an acetal or ketal of glycerol (hereinafter called "protected glycerol") to obtain a 1,3-dioxolane compound (III) and then subjecting the 1,3-dioxolane compound (III) to hydrolysis, whereby resulting in the completion of this invention.

The process according to this invention is represented by the following reaction formula:

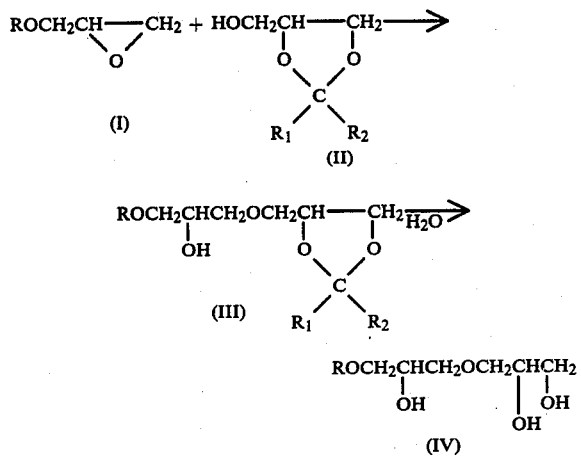

wherein R, $R_1$ and $R_2$ are as defined above.

DETAILED DESCRIPTION OF PREFERRED EMBODIMENTS

The alkyl glycidyl ether used in this invention is a glycidyl ether having a primary, secondary or tertiary, straight or branched chain, saturated or unsaturated, aliphatic hydrocarbon group having 8–24 carbon atoms. Specific examples of such a glycidyl ether include straight chain, primary alkyl glycidyl ethers such as n-octyl glycidyl ether, n-decyl glycidyl ether, n-dodecyl glycidyl ether, n-tetradecyl glycidyl ether, n-hexadecyl glycidyl ether, n-octadecyl glycidyl ether, n-octadecenyl glycidyl ether (oleyl glycidyl ether) and docosyl glycidyl ether; branched, primary alkyl glycidyl ethers such as 2-ethylhexyl glycidyl ether, 2-hexyldecyl glycidyl ether, 2-octyldodecyl glycidyl ether, 2-heptylundecyl glycidyl ether, 2-(1,3,3-trimethylbutyl)octyl glycidyl ether, 2-decyltetradecyl glycidyl ether, 2-tetradecyloctadecyl glycidyl ether, 2-dodecylhexadecyl glycidyl ether, 5,7,7-trimethyl-2-(1,3,3-timethylbutyl)octyl glycidyl ether, and primary alkyl glycidyl ethers such as a methyl-branched isostearyl glycidyl ether mixture represented by the following formula:

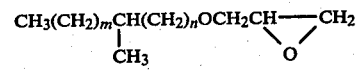

wherein m and n are both integers and range respectively from 4 to 10 and from 5 to 11, m+n ranges from 11 to 17, and the mixture is distributed in its components with a peak at m=7 and n=8; secondary alkyl glycidyl ethers such as sec.-decyl glycidyl ether, sec.-octyl glycidyl ether and sec.-dodecyl glycidyl ether; and tertiary alkyl glycidyl ethers such as t-octyl glycidyl ether and t-dodecyl glycidyl ether.

Incidentally, new processes have been developed recently to produce with a high yield alkyl glycidyl ethers from their corresponding alcohols (ROH) without need for isolating halohydrin ethers (see, for example, Japanese Patent Laid-open Nos. 76508/1979, 141708/1979, 141709/1979 and 141710/1979). Thus, these alkyl glycidyl ethers may also be used as raw materials.

Exemplary protected glycerols (II) include acetals and ketals of glycerol, which are respectively derived from aldehydes and ketones. As specific examples of compounds adapted to form protecting groups, in other words, as exemplary aldehydes for yielding acetals, may be mentioned aliphatic aldehydes (formaldehyde, acetaldehyde, propionaldehyde, octylaldehyde, etc.), alicyclic aldehydes (cyclopentylaldehyde, cyclohexylaldehyde, etc.) and aromatic aldehyde (benzaldehyde, naphthylaldehyde, etc.). On the other hand, as exemplary ketones for deriving ketals, may be mentioned aliphatic ketones (acetone, methyl ethyl ketone, diethyl ketone, methyl propyl ketone, dipropyl ketone, ethyl propyl ketone, methyl hexyl ketone, etc.), alicyclic ketones (cyclobutanone, cyclopentanone, cyclohexanone, cyclooctanone, etc.) and aromatic ketones (acetophenone, benzophenone, etc.). Protected glycerols may be produced from these compounds and glycerol by subjecting in the presence of an acidic catalyst glycerol and the above ketones or aldehydes to a dehydration and condensation reaction in accordance with any known method.

As catalysts usable for the reaction between an alkyl glycidyl ether (I) and protected glycerol (II), there may be mentioned basic catalysts such as alkali metal hydroxides (for example, LiOH, NaOH, KOH, etc.), alkali metal alcoholates (for example, NaOMe, NaOEt, t-BuOK, etc.) and tertiary amines (for example, triethylamine, tributylamine, tetramethylethylene diamine, tetramethyl-1,3-diaminopropane, tetramethyl-1,6-diaminohexane, triethylene diamine, etc.); and acidic catalysts such as protonic acids including sulfuric acid, hydrochloric acid, nitric acid, phosphoric acid, etc., and Lewis acids such as boron trifluoride-ether complex, boron trifluoride-acetic acid complex, boron trifluoride-phenol complex, aluminum chloride, aluminum bromide, zinc chloride, tin tetrachloride, antimony chloride, titanium tetrachloride, silicon tetrachloride, ferric chloride, ferric bromide, cobaltic chloride, cobaltic bromide, zirconium chloride, boron oxide and acidic activated alumina.

The above reaction can generally be carried out by reacting 1 mole of an alkyl glycidyl ether (I) with 1–10, preferably, 1–5 moles of a protected glycerol (II) in the presence of 0.001–0.2, particularly preferably, 0.01–0.1 mole of a catalyst at 70°–150° C., particularly preferably, 90°–120° C.

The protected glycerol (II) may theoretically be used in the same molar amount as the alkyl glycidyl ether (I). Practically speaking, a better yield is available and the reaction proceeds in a shorter period of time if the protected glycerol (II) is used in a amount greater than the equimolar amount. Although the reaction may proceed without any reaction solvent, it is most preferable to use the protected glycerol (II) in such an excess amout that it also serves as a solvent. It is also possible to use a solvent if necessary. As a reaction solvent, any solvent may be employed so long as it does not affect adversely on the reaction, but a hydrocarbon solvent is preferred. Exemplary hydrocarbon solvents may include aliphatic hydrocarbons such as pentane, hexane, heptane and octane, aromatic hydrocarbons such as benzene, toluene and xylene, alicyclic hydrocarbons such as cyclopentane and cyclohexane, and mixtures thereof.

By carrying out the reaction as described above, a 1,3-dioxolane compound (III) may be obtained with a yield of 80% or higher. The resulting 1,3-dioxolane compound (III) may then be purified by virtue of distillation or the like. It can however be subjected to the subsequent hydrolysis reaction as is without need for isolation and purification since it is generally obtained as a colorless, odor-free, clear liquid.

The hydrolysis reaction of the 1,3-dioxolane compound (III) may be effected in accordance with any known method. It is however preferred to carry out the hydrolysis reaction by heating the 1,3-dioxolane compound (III) in water using a protonic acid catalyst such as sulfuric acid, hydrochloric acid, nitric acid, phosphoric acid, benzenesulfonic acid or acetic acid. There is no particular limitation vested to the amount of such an acid catalyst. It is sufficient in quantity if used in an amount of 0.01–2N. Especially, it is suitable to use the acid catalyst in the range of 0.05–1.0N. Water may be added with a water-soluble organic solvent, for example, a lower alcohol such as methanol, ethanol or isopropanol, THF, dioxane or the like. The reaction temperature may preferably range from 50° to 100° C.

Upon carrying out the hydrolysis reaction under such conditions, the intended product, α-monoalkyl ether (IV) of diglycerol is obtained in a stoichiometrical amount from its corresponding 1,3-dioxolane compound (III).

It has been confirmed that the α-monoalkyl ether (IV) of diglycerol resulted in accordance with the above process of this invention has the same structure as that synthesized in accordance with the above-mentioned known process (3). In other words, the α-monoalkyl ether of diglycerol according to the present invention was identical in both physical properties and spectrum data with the α-monoalkyl ether of diglycerol, the latter α-monoalkyl ether having been obtained by reacting in the presence of a catalytic amount of a basic or acidic substance the alcohol (VI) with 2,2-dimethyl-4-(2′,3′-epoxy)propoxymethyl-1,3-dioxolane (V) in accordance with the procedure employed in Comparative Example 3 or 5, isolating the principal reaction product, 1,3-dioxolane compound (III′) and subjecting it to hydrolysis. Thus, it has been confirmed that the diglyceryl ether obtained in accordance with the process of this invention can be represented by the following general formula:

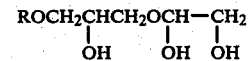

wherein R has the same significance as defined above.

Among the above-described compounds, 2,2-dimethyl-4-(2′,3′-epoxy)propoxymethyl-1,3-dioxolane (V) is a known compound and can be prepared by subjecting an epihalohydrin and glycerol acetone ketal to a dehydrohalogenation reaction in accordance with the following reaction formula (Journal f. Prakt. Chemie, Band 316, PP325–336 (1974); refer to Comparative Example 1):

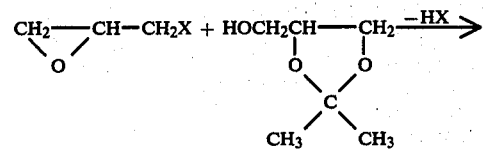

-continued

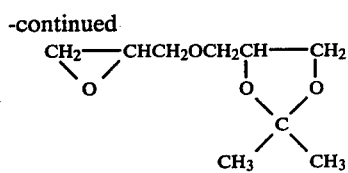

wherein X is as defined above.

The catalyst and hydrolysis method employed in the preparation of an α-monoalkylether of diglycerol in accordance with the process of this invention may be applied, as they are, as a catalyst and hydrolysis method to be used in Comparative Example 3 or 5.

The invention will hereinafter be described in more detail with reference to the following examples, referential examples and comparative examples. However, it shall be noted that the present invention is not limited to such examples.

REFERENTIAL EXAMPLE 1

Into a 1 l, round bottomed flask equipped with a reflux condenser, thermometer, dropping funnel and stirrer, were added 120 g of a 50% aqueous solution of sodium hydroxide (60 g, i.e., 1.5 moles as pure sodium hydroxide), 68 g (0.25 mole) of monomethyl-branched isostearyl alcohol obtained in Referential Example 2, 200 ml of n-hexane and 2.51 g (0.0075 mole) of stearyl trimethylammonium chloride sequentially in the order as they appear. While maintaining the reaction mixture at a reaction temperature of 25° C. in a water bath and agitating it at a stirring speed of 400 rpm, were dropped 93 g (1 mole) of epichlorohydrin. After adding dropwise epichlorohydrin over about 1.5 hours, the reaction mixture was heated to 50° C. and agitated at the same temperature for approximately further 8 hours. Upon completion of the reaction, the resultant reaction mixture was treated in accordance with procedures commonly employed, resulting in the provision of 68 g of monomethyl-branched isostearyl glycidyl ether represented by a formula given below (yield: 83%).

Boiling point: 142°–175° C. (0.08 mmHg).
IR (liquid film, cm$^{-1}$): 3050, 3000, 1250, 1100, 920, 845.

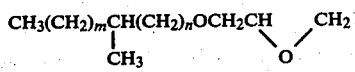

wherein m and n represent integers and range respectively from 4 to 10 and from 5 to 11, m+n ranges from 11 to 17, and the ether is distributed in its components with a peak at m=7 and n=8.

REFERENTIAL EXAMPLE 2

In a 20 l autoclave, were charged 4770 g of isopropyl isostearate, ("Emery 2310", isopropyl isostearate, commercially available from Emery Corporation, U.S.A.) and 239 g of a copper-chromium catalyst (product of JGC Corporation). Then, the autoclave was filled with hydrogen gas to a pressure of 150 kg/cm$^2$. The reaction mixture was thereafter heated to 275° C. Hydrogen was blown into the autoclave for about 7 hours while maintaining the reaction system at 150 kg/cm$^2$ and 275° C. Upon cooling the reaction product and removing catalyst residue through filtration, 3500 g of a crude reaction product was obtained. By distilling the crude reaction product under reduced pressures, 3300 g of colorless, clear isostearyl alcohol was obtained as a fraction at 80°–167° C./0.6 mmHg. The thus-obtained isostearyl alcohol (monomethyl-branched isostearyl alcohol) had an acid value of 0.05, saponification value of 5.5 and hydroxyl value of 181.4. Its IR (liquid film) spectrum contained absorptions respectively at 3340 and 1055 cm$^{-1}$, while absorptions occurred at δ3.50 (broad triplet, —CH$_2$—OH) in its NMR analysis (CCl$_4$ solvent). It was found from a gas chromatographic analysis of the above alcohol that its main component contained 18 carbon atoms as the total number of carbon atoms of its alkyl group and amounted to about 75% and the remainder was a mixture of those containing 14 and 16 carbon atoms as the total numbers of carbon atoms of their alkyl groups and having their pendant methyl groups near the centers of their main alkyl chains.

EXAMPLE 1

(i) Into a 5 l, round bottomed flask equipped with a reflux condenser, thermometer, dropping funnel, nitrogen gas-feeding tube and stirrer, were charged 1061 g (8 moles) of glycerol dimethyl ketal and 28.4 g (0.165 mole) of tetramethyl-1,6-diaminohexane, which were then agitated and mixed while aerating the flask with nitrogen gas. Under the nitrogen gas aeration, 1308 g (4 moles) of the monomethyl-branched isostearyl glycidyl ether obtained in Referential Example 1 was dropped little by little through the dropping funnel. While the dropwise addition of the glycidyl ether, the reaction mixture was heated and maintained at 100° C. or so. The glycidyl ether was added in the course of about 2 hours. In the course of the addition of the glycidyl ether, the temperature of the reaction mixture increased little by little and reached 125° C. when the dropwise addition of the glycidyl ether was finished. The resultant reaction mixture was continuously heated and agitated for approximately further 6 hours at reaction temperatures of from 130° to 140° C. After verifying from a gas chromatographic diagram of the reaction mixture that the isostearyl glycidyl ether was completely used up, the reaction product was cooled down to room temperature. Then, 1500 g of city water and 100 g of salt were sequentially added to the reaction product. The resultant mixture was allowed to stand until it was separated into layers. The upper layer was collected and dried with anhydrous sodium sulfate, followed by the separation through distillation under reduced pressures of glycerol dimethyl ketal which was employed excessively. The resulting mixture wsas subjected to a further distillation under reduced pressures, thereby obtaining 2,2-dimethyl-4-(2'-hydroxy-3'-isostearoxy)propoxymethyl-1,3-dioxolane in an amount of 1510 g (yield: 82%).

Boiling point: 210°–230° C. (0.5–0.8 mmHg).
Elemental analysis: Calculated for C$_{27}$H$_{54}$O$_5$: C,70.62; H,11.85; O,17.42. Found: C,70.7; H,12.1; O,16.9.
IR (liquid film, cm$^{-1}$): 3460, 1380, 1370, 1260, 1210, 1115, 1055, 850.
NMR (CCl$_4$ solvent, δ): 3.2–4.3 (multiplet, 12H;

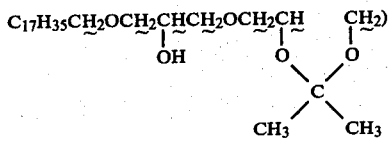

-continued 1.3 (singlet, 6H; 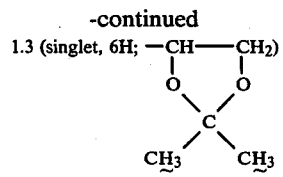

Acid Value: 0.01 (calculated acid value: 0.0);
Saponification value: 1.5 (calculated saponification value: 0.0);
Hydroxyl value: 120 (calculated hydroxyl value: 122);
Iodine value: 1.0 (calculated iodine value: 0.0);
Oxirane oxygen: 0% (calculated oxirane value: 0%); and
Molecular weight (determined by the VPO method in CHCl$_3$): 458 (calculated molecular weight: 459).

(ii) In a 2 l reaction vessel equipped with a stirrer, thermometer and reflux condenser, was charged 251 g (0.347 mole) of the 1,3-dioxolane compound obtained in the above experiment (i), followed by a further addition of 230 ml of methanol and 300 ml of 1N-sulfuric acid. The mixture was heated and refluxed at 75°–80° C. while stirring the same. About 5 hours later, an gas chromatographic analysis showed that the hydrolysis of the 1,3-dioxolane compound was carried out completely. After allowing the reaction mixture to cool down to room temperature, it was allowed to stand and separate into an oil and water layers. The oil layer was collected. Subsequent to adding 500 ml of ether into the water layer, the resultant mixture was thoroughly shaken and then allowed to stand. The resultant ether layer was collected and combined with the oil layer which was previously obtained. The solvents were driven off under reduced pressures and the resultant substance was heated and dried for 3 hours at 100° C. and 0.1 mmHg, leading to 220 g of colorless, clear and syrupy 2-hydroxy-3-isostearoxypropyl glyceryl ether (yield: 96%).

Elementary analysis: Calculated for C$_{24}$H$_{50}$O$_5$: C, 68.77; H, 12.02; O, 19.08. Found: C, 68.4; H, 12.1; O, 19.2.

IR (liquid film, cm$^{-1}$): 3360, 1105, 1040.
NMR (CCl$_4$ solvent, δ): 3.2–3.8 (multiplet, 12H;

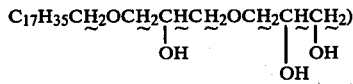

Acid value: 0.1 (theoretical value: 0.0);
Saponification value: 0.5 (theoretical value: 0.0);
Hydroxyl value: 400 (theoretical value: 402);
Iodine value: 0.5 (theoretical value: 0); and
Molecular weight (determined by the VPO method in CHCl$_3$): 420 (calculated molecular weight: 419).

EXAMPLE 2

(i) The procedures of Experiment (i) in Example 1 were followed, except for the substitution of 24.3 g (0.165 mole) of 47% boron trifluoride-diethyl ether complex for tetramethyl-1,6-diaminohexane and the adoption of reaction temperatures of 85°–90° C. The reaction product was neutralized and separated into a water and oil layers. The oil layer was collected and then subjected to distillation under reduced pressures, thereby obtaining 1450 g of 2,2-dimethyl-4-(2'-hydroxy-3'-methyl-branched isostearoxy)propoxymethyl-1,3-dioxolane (yield: 79%). Its boiling point, and IR and NMR spectra were identical to those of 2,2-dimethyl-4-(2'-hydroxy-3'-isostearoxy)propoxymethyl-1,3-dioxolane obtained in Experiment (i) of Example 1.

Acid value: 0.02 (calculated acid value: 0.0);
Saponification value: 1.0 (calculated saponification value: 0.0);
Hydroxyl value: 125 (calculated hydroxyl value: 122);
Iodine value: 0.5 (calculated iodine value: 0.0); and
Oxirane oxygen: 0% (calculated value: 0%).

(ii) A hydrolysis reaction was carried out under the same conditions as those employed in Experiment (ii) of Example 1, whereby obtaining 225 g of colorless, clear, syrupy 2-hydroxy-3-isostearoxypropyl glyceryl ether (yield: 98%). Its IR and NMR spectra were identical to those obtained in Experiment (ii) of Example 1.

Acid value: 0.1 (calculated acid value: 0.0);
Saponification value: 0.3 (calculated saponification value: 0.0);
Hydroxyl value: 401 (calculated hydroxyl value: 402); and
Iodine value: 0.3 (calculated iodine value: 0.0).

EXAMPLE 3

Into a 1 l reaction vessel equipped with a reflux condenser, thermometer, dropping funnel and stirrer, were charged 298 g (2.25 moles) of acetone glycerol ketal and 12.9 g (0.075 mole) of tetramethyl diaminohexane. They were mixed together. The reaction mixture was heated to 100° C., to which was slowly dropped 140 g (0.75 mole) of octyl glycidyl ether. The temperature of the reaction mixture was maintained at 100°–110° C. during the dropwise addition of the glycidyl ether, which took about 30 minutes. The reaction mixture was then heated for 6 hours at 100°–110° C. After cooling, excess acetone glycerol ketal was distilled off under reduced pressures from the reaction product. Upon subjecting the residue to distillation under reduced pressures, 203 g of a colorless, clear liquid was resulted (yield: 85%). The liquid produced a single peak on a gas chromatographic spectrum, whereby confirming that it was 2,2-dimethyl-4-(2'-hydroxy-3'-octoxy)propoxymethyl-1,3-dioxolane.

Boiling point: 172°–175° C. (0.6 mmHg);
Elementary analysis: Calculated for C$_{17}$H$_{34}$O$_5$: C, 64.12; H, 10.76; O, 25.12. Found: C, 63.9; H, 10.8; O, 24.7.

IR (liquid film, cm$^{-1}$): 3470, 1380, 1370, 1255, 1212, 1110, 1080, 1050, 840.
NMR (CCl$_4$ solvent, δ):

3.3–4.4 (multiplet, 13H,

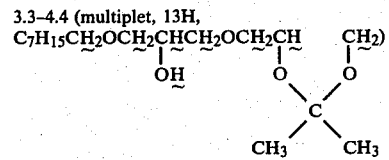

1.37 (singlet, 6H,

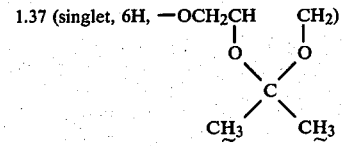

1.4 (singlet, 12H, CH$_3$(CH$_2$)$_6$CH$_2$O—)

0.95 (triplet, 3H, CH₃(CH₂)₆CH₂O—)

Acid value: 0.01;
Saponification value: 0.03;
Hydroxyl value: 180 (calculated hydroxyl value: 176);
Iodine value: 0.1;
Oxirane oxygen: 0%; and
Molecular weight (determined by the VPO method in CHCl₃): 318 (calculated molecular weight: 318).

(ii) Into a 1 l reaction vessel equipped with a reflux condenser, thermometer and agitator, were charged 200 ml of water and 10.1 g of 97% conc. sulfuric acid. They were vigorously mixed into a 1N-aqueous sulfuric acid solution, to which 63.6 g (0.2 mole) of the 1,3-dioxolane compound obtained in the above Experiment (i) and 150 ml of ethanol were added in the order as they appear. The resultant mixture was heated. The reaction mixture looked in the beginning like a milky white emulsion but, as soon as it was refluxed, it turned to a clear, homogeneous solution. After refluxing the reaction mixture for about 4 hours with heating, the reaction mixture was cooled and neutralized with 8.3 g of 97% sodium hydroxide. After the neutralization, it was combined with 300 ml of ether and extracted. Subsequent to allowing it to separate into layers, the ether layer was collected. It was dried with anhydrous sodium sulfate and then subjected to distillation under reduced pressures to drive off ether. After distilling off ether, the resultant substance was dried further at 0.1 mmHg and about 100° C. and for about 3 hours, thereby obtaining 54.9 g of a colorless, clear, slightly viscous liquid (yield: 98.7%). Its gas chromatographic analysis confirmed that it consisted of a single component, 2-hydroxy-3-octoxypropyl glyceryl ether.

Elementary analysis: Calculated for C₁₄H₃₀O₅: C, 60.40; H, 10.86; O, 28.73. Found: C, 60.0; H, 10.9; O, 28.6.

IR (liquid film, cm⁻¹): 3380, 1170–1000, 875.
NMR (CCl₄ solvent, δ):

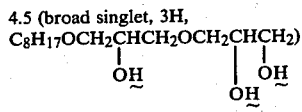
4.5 (broad singlet, 3H, C₈H₁₇OCH₂CHCH₂OCH₂CHCH₂)
           |            |    |
          OH           OH   OH

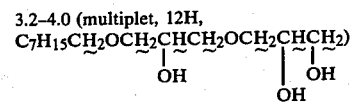
3.2–4.0 (multiplet, 12H, C₇H₁₅CH₂OCH₂CHCH₂OCH₂CHCH₂)
                |            |    |
               OH           OH   OH

1.3 (singlet, 12H, CH₃(CH₂)₆CH₂O—)

0.88 (triplet, 3H, CH₃(CH₂)₆CH₂O—)

Acid value: 0.05;
Saponification value: 0.06;
Hydroxyl value: 595 (calculated saponification value: 605);
Iodine value: 0.5; and
Molecular weight (determined by the VPO method in CHCl₃): 280 (calculated molecular weight: 278).

EXAMPLE 4

(i) The procedures of Experiment (i) in Example 3 were followed to carry out a reaction, except for the substitution of 182 g (0.75 mole) of dodecyl glycidyl ether for octyl glycidyl ether. Upon conducting post treatments in the same manner, 230 g of a colorless, clear liquid was resulted (yield: 82%). Its gas chromatographic analysis confirmed that it consisted of a single component, 2,2-dimethyl-4-(2'-hydroxy-3'-dodecyloxy)propoxymethyl-1,3-dioxolane.

Boiling point: 196°–200° C. (0.5 mmHg);
Elementary analysis: Calculated for C₂₁H₄₂O₅: C, 67.34; H, 11.30; O, 21.36. Found: C, 67.0; H, 11.4; O, 21.1.

IR (liquid film, cm⁻¹): 3470, 1380, 1370, 1255, 1213, 1140, 1080, 1050, 845.
NMR (CCl₄ solvent, δ):

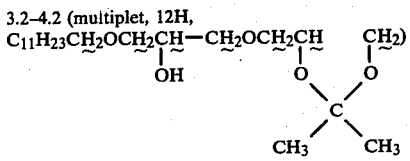
3.2–4.2 (multiplet, 12H, C₁₁H₂₃CH₂OCH₂CH—CH₂OCH₂CH   CH₂)
                              |               |    |
                             OH               O    O
                                               \  /
                                                C
                                               / \
                                             CH₃  CH₃

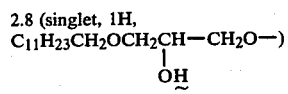
2.8 (singlet, 1H, C₁₁H₂₃CH₂OCH₂CH—CH₂O—)
                            |
                           OH

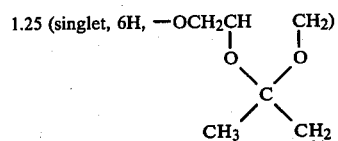
1.25 (singlet, 6H, —OCH₂CH   CH₂)
                        |    |
                        O    O
                         \  /
                          C
                         / \
                       CH₃  CH₃

1.20 (singlet, 20H, CH₃(CH₂)₁₀CH₂O—)

0.87 (triplet, 3H, CH₃(CH₂)₁₀CH₂O—)

Acid value: 0.0;
Saponification value: 0.05;
Hydroxyl value: 155 (calculated hydroxyl value: 150);
Iodine value: 0.3;
Oxirane oxygen: 0%; and
Molecular weight (determined by the VPO method in CHCl₃): 376 (calculated molecular weight: 375).

(ii) A hydrolysis was effected under the same conditions as those employed in Experiment (ii) of Example 3, except for the employment of 76.4 g (0.2 mole) of 2,2-dimethyl-4-(2'-hydroxy-3'-dodecyloxy)propoxymethyl-1,3-dioxolane obtained in the above Experiment (i) as a 1,3-dioxolane compound. The reaction product was post-treated in the same manner, thereby yielding 66 g of a colorless, clear, viscous liquid (yield: 98.7%). It was allowed to cool down, thereby turning to a white solid. Its gas chromatographic analysis confirmed that the above substance consisted of a single component, 2-hydroxy-3-dodecyloxypropyl glyceryl ether.

Melting point: 42°–44° C.;
Elementary analysis: Calculated for C₁₈H₃₈O₅: C, 64.63; H, 11.45; O, 23.92 Found: C, 64.3; H, 11.2; O, 23.5.

IR (liquid film, cm⁻¹): 3380, 1170–1000, 880.
NMR (CCl₄ solvent, δ):

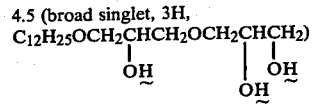
4.5 (broad singlet, 3H, C₁₂H₂₅OCH₂CHCH₂OCH₂CHCH₂)
                                |            |    |
                               OH           OH   OH -continued 3.2–4.0 (multiplet, 12H,
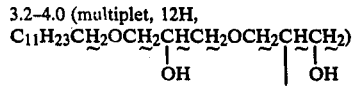
)

1.3 (singlet, 20H, CH$_3$(CH$_2$)$_{10}$CH$_2$O—)

0.9 (triplet, 3H, CH$_3$(CH$_2$)$_{10}$CH$_2$O—)

Acid value: 0.03;
Saponification value: 0.1;
Hydroxyl value: 495 (calculated hydroxyl value: 502);
Iodine value: 0.1; and
Molecular weight (determined by the VPO method in CHCl$_3$): 334 (calculated molecular weight: 335).

COMPARATIVE EXAMPLE 1

Into a 500 ml reaction vessel furnished with a thermometer, stirrer, reflux condenser and dropping funnel, were placed 184 g (2 moles) of glycerol and 1.72 g (0.01 mole) of tetramethyl-1,6-diaminohexane. They were heated to 100° C. with stirring. Then, while aerating the reaction vessel with nitrogen gas, 65.4 g (0.2 mole) of the monomethyl-branched isostearyl glycidyl ether obtained in Referential Example 1 was added slowly. The reaction system was first in a light yellowish, uneven state. Its viscosity increased gradually as time went on. About 8 hours later, it turned to a thick, creamy mixture. During the reaction, the reaction mixture was maintained at 100°–120° C. After confirming through a gas chromatographic analysis that the glycidyl ether was completely used up, the reaction product was cooled down to room temperature, to which 400 ml of water, 500 ml of ether and 50 g of sodium chloride were added sequentially in the order as they appear. The resulting mixture was vigorously agitated. It was then separated into layers. The ether layer was collected and, subsequent to drying the same with anhydrous sodium sulfate, ether was distilled off under reduced pressures. By further heating the residual substance under reduced pressure (100° C./0.1 mmHg), 75 g of a syrupy, yellowish brown solution was obtained. Its analytical fat data were as follows:

Acid value: 0.03;
Saponification value: 1.5;
Hydroxyl value: 280 (calculated hydroxyl value: 402);
Iodine value: 1.0; and
Oxirane oxygen: 0%.

COMPARATIVE EXAMPLE 2

A reaction was carried out under the same conditions as those employed in Comparative Example 1, except for the employment of 350 ml of dimethyl formamide as its reaction solvent, resulting in the provision of 68 g of a yellowish brown, syrupy solution. Its analytical fat data were as follows:

Acid value: 0.2;
Saponification value: 6.0;
Hydroxyl value: 180 (calculated hydroxyl value: 402)
Iodine value: 0.5; and
Oxirane oxygen: 0%

COMPARATIVE EXAMPLE 3

Into a 3 l reaction vessel equipped with a reflux condenser, thermometer, dropping funnel and agitator, were charged 720 g of a 50% aqueous sodium hydroxide solution (360 g, i.e., 9 moles as sodium hydroxide), 400 g of hexane and 397 g (3 moles) of acetone glycerol ketal. They were vigorously agitated. After adding 39.6 g (0.15 mole) of trimethyldodecylammonium chloride, the reaction mixture was maintained at 30° C., followed by a dropwise gradual addition of 555 g (6 moles) of epichlorohydrin from the dropping funnel. The dropwise addition of epichlorohydrin was completed in about 2 hours. Thereafter, the reaction mixture was heated to 50° C., where it was continuously agitated with heating for about 2 hours as it was. The resultant reaction product was cooled and allowed to separate into layers. The hexane layer was collected and, after drying it with anhydrous sodium sulfate, hexane was distilled off. Upon subjecting the residual substance to distillation under reduced pressured, the intended product, 2,2-dimethyl-4-(2′,3′-epoxy)propoxymethyl-1,3-dioxolane was obtained in an amount of 440 g (yield: 78%). Boiling point: 91°–94° C. (2.5 mmHg) (92°–94° C./2.5 mmHg in publications).

COMPARATIVE EXAMPLE 4

(i) Into a 1 l reaction vessel furnished with a reflux condenser, thermometer, dropping funnel and stirrer, were charged 117 g (0.9 mole) of octyl alcohol and 5.2 g (0.03 mole) of tetramethyl diaminohexane. They were heated to 100° C. and agitated, followed by a gradual dropwise addition of 56.5 g (0.3 mole) of 2,2-dimethyl-4-(2′,3′-epoxy)propoxymethyl-1,3-dioxolane obtained in the above Comparative Example 3 through the dropping funnel. During the dropping, the reaction mixture was maintained at 100°–110° C. They were allowed to react at the above temperatures for about 6 hours. The reaction product was cooled and neutralized with a dilute hydrochloric acid, followed by a collection of the organic layer. The organic layer was then subjected to distillation under reduced pressures, thereby obtaining 29 g of a colorless, clear liquid (yield: 31%). Its boiling point and gas chromatograph, IR and NMR spectra were identical to their corresponding data of the 1,3-dioxolane compound obtained in Experiment (i) of Example 3, which relates to the present invention.

(ii) The dioxolane compound resulted in the above Experiment (i) was subjected to hydrolysis in accordance with the procedures employed in Experiment (ii) of Example 3 of the present invention, thereby obtaining the intended product, 2-hydroxy-3-octoxypropyl glyceryl ether (yield: 98%). Its gas chromatograph, IR and NMR spectra were identical to their corresponding data of the diglycerol octyl ether compound obtained in Experiment (ii) of Example 3 of this invention.

COMPARATIVE EXAMPLE 5

(i) A reaction was carried out under the same conditions as those employed in Experiment (i) of Comparative Example 4, except for the substitution of 4.2 g (0.03 mole) of boron trifluoride-ether complex for the catalyst, tetramethyl diaminohexane. Through a distillation under reduced pressures, 33.4 g of a colorless, clear liquid was obtained (yield: 35%). Its boiling point and gas chromatography, IR and NMR spectra were identical to their corresponding data of the 1,3-dioxolane compound obtained in Experiment (i) of Example 3 of this invention.

(ii) The 1,3-dioxolane compound obtained in the above Experiment (i) was subjected to hydrolysis in accordance with the procedures employed in Experiment (ii) of Example 3 of this invention, thereby obtaining the intended product, 2-hydroxy-3-octoxypropyl glyceryl ether (yield: 98%). Its gas chromatography, IR and NMR spectra were identical to their corresponding data of diglycerol octyl ether obtained in Experiment (ii) of Example 3 of this invention.

What is claimed is:

1. A process for preparing a 2-hydroxy-3-alkoxypropylglyceryl ether represented by the general formula (IV):

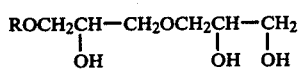 (IV)

wherein R is a saturated or unsaturated, straight or branched chain, aliphatic hydrocarbon group having 8–24 carbon atoms, which process comprises reacting in the presence of an acidic or basic catalyst an alkylglycidyl ether represented by the general formula (I):

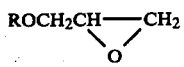 (I)

wherein R is as defined above with an acetal or ketal derivative of glycerol which derivative is represented by the general formula (II):

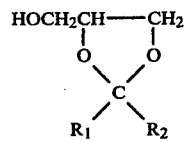 (II)

wherein $R_1$ and $R_2$ are individually a hydrogen atom or a lower alkyl, aryl or aralkyl group to obtain a 4-(2'-hydroxy-3'-alkoxy)propoxymethyl-1,3-dioxolane represented by the general formula (III):

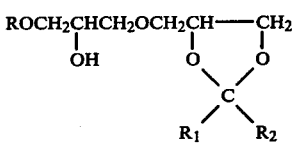 (III)

wherein R, $R_1$ and $R_2$ are as defined above; and then subjecting the thus-obtained 4-(2'-hydroxy-3'-alkoxy)-propoxymethyl-1,3-dioxolane to hydrolysis.

2. The process according to claim 1, wherein the hydrolysis is effected in the presence of a protonic acid catalyst.

3. The process according to claim 1, wherein the hydrolysis is effected in a medium obtained by adding a water-soluble organic solvent to water.

4. The process according to claim 1, wherein R is a saturated or unsaturated, straight or branched chain, aliphatic hydrocarbon group having 12–20 carbon atoms.

5. The process according to claim 1, characterized in that the alkyl glycidyl ether and the acetal or ketal derivative are reacted in a molar ratio of 1:1–10, the acidic or basic catalyst is employed in an amount of 0.001–0.2 mole, and the reaction temperature is 70°–150° C.

* * * * *